Dec. 24, 1963 G. AUVIL Plant Pat. 2,334

APPLE TREE

Filed Sept. 22, 1961 3 Sheets-Sheet 1

INVENTOR
GRADY AUVIL

BY
Reynolds & Christensen
ATTORNEYS

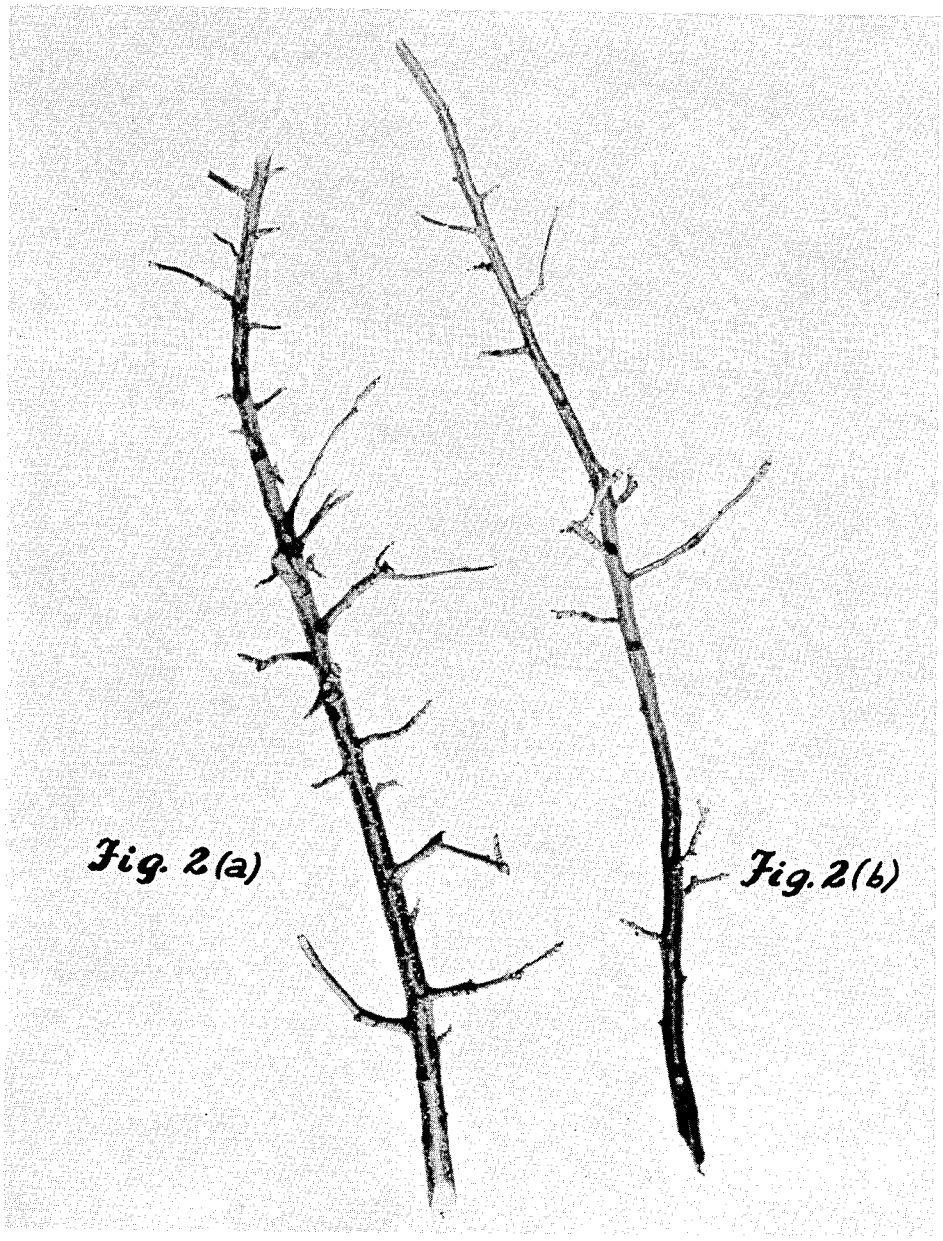
INVENTOR
GRADY AUVIL
BY Reynolds & Christensen
ATTORNEYS

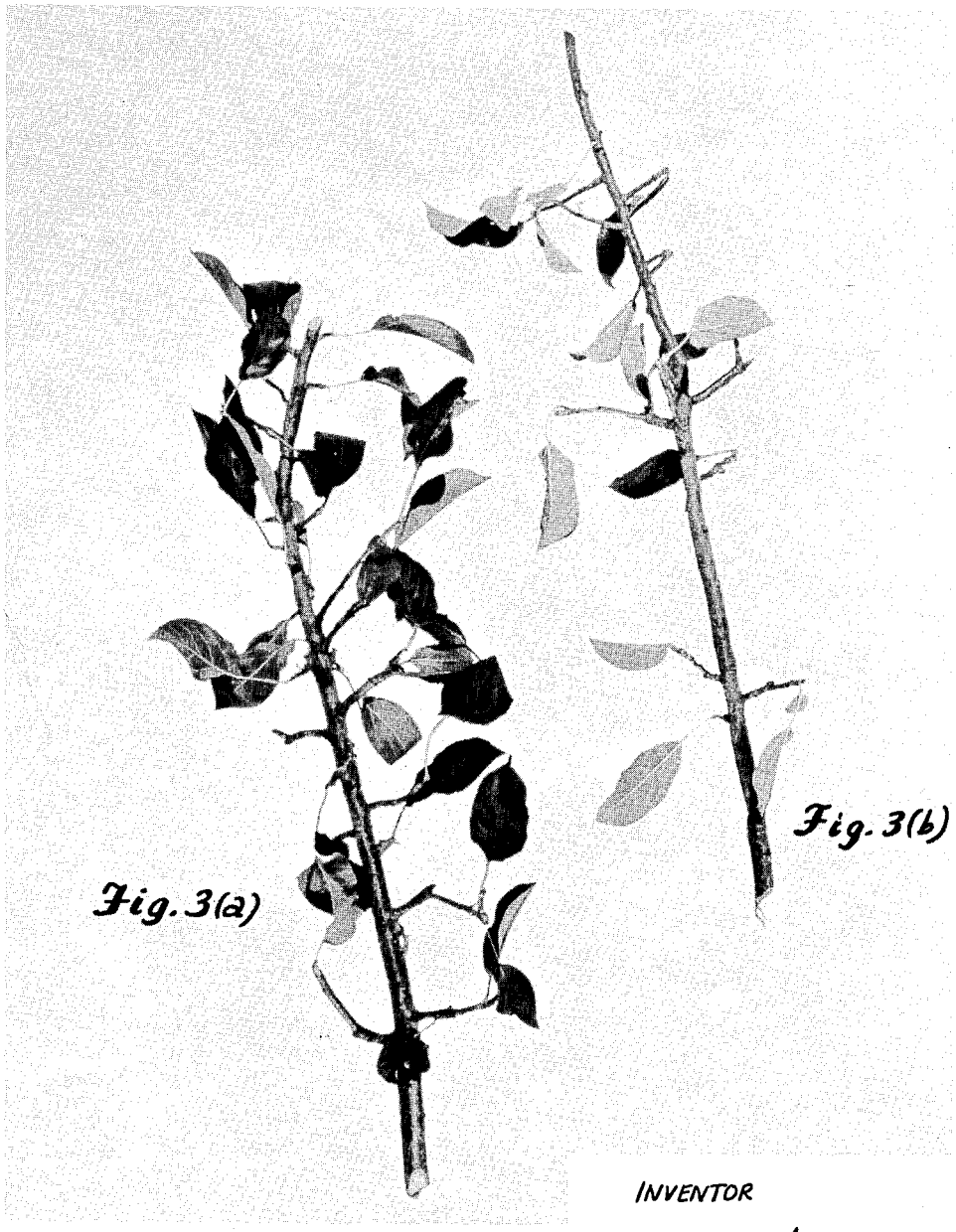
INVENTOR
GRADY AUVIL
By Reynolds & Christensen
ATTORNEYS

United States Patent Office

Plant Pat. 2,334
Patented Dec. 24, 1963

2,334
APPLE TREE

Grady Auvil, Orondo, Wash., assignor to Sundale Orchards, Inc., Roosevelt, Wash., a corporation of Washington Filed Sept. 22, 1961, Ser. No. 140,140
1 Claim. (Cl. Plt.—35)

This invention or discovery relates to a new and distinct variety of apple tree originating as a bud sport of the variety which has long been sold in commerce under the name "Golden Delicious" (unpatented), the discovery having been made in my cultivated orchard near Roosevelt, Klickitat County, Washington.

The new variety is of semi-dwarf growth which makes it possible to plant at shorter distances than can be done with its parent variety. The tree differs from its parent not only in size but in the outstanding spurred condition of its branches, having a much greater number of fruit spurs per unit length of wood than on the parent variety. In addition to these distinguishing characteristics my new variety also shows a pronounced trait of setting a much greater number of fruits per cluster. By actual count I found on the average twice as many fruits for each fruiting spur as those on adjacent trees of standard Golden Delicious. The outstanding clustering characteristic makes my new variety a heavier bearer and one which produces fruit of more uniform size. This is a distinct market advantage, having a greater percentage of fruits in the most desirable marketable sizes.

I have asexually reproduced my new variety in my orchards near Orondo, Douglas County, Washington, by means of grafting, and its outstanding characteristics appear to be permanent.

FIGURE 2(*a*) is a photograph of a typical branch of the new variety (leaves removed) showing the large number of spurs per unit length of branch, while FIGURE 2(*b*) is a photograph of a typical Golden Delicious branch (leaves removed) for purposes of comparison, both branches being taken from trees growing under the same conditions in Roosevelt, Washington.

Figure 1:
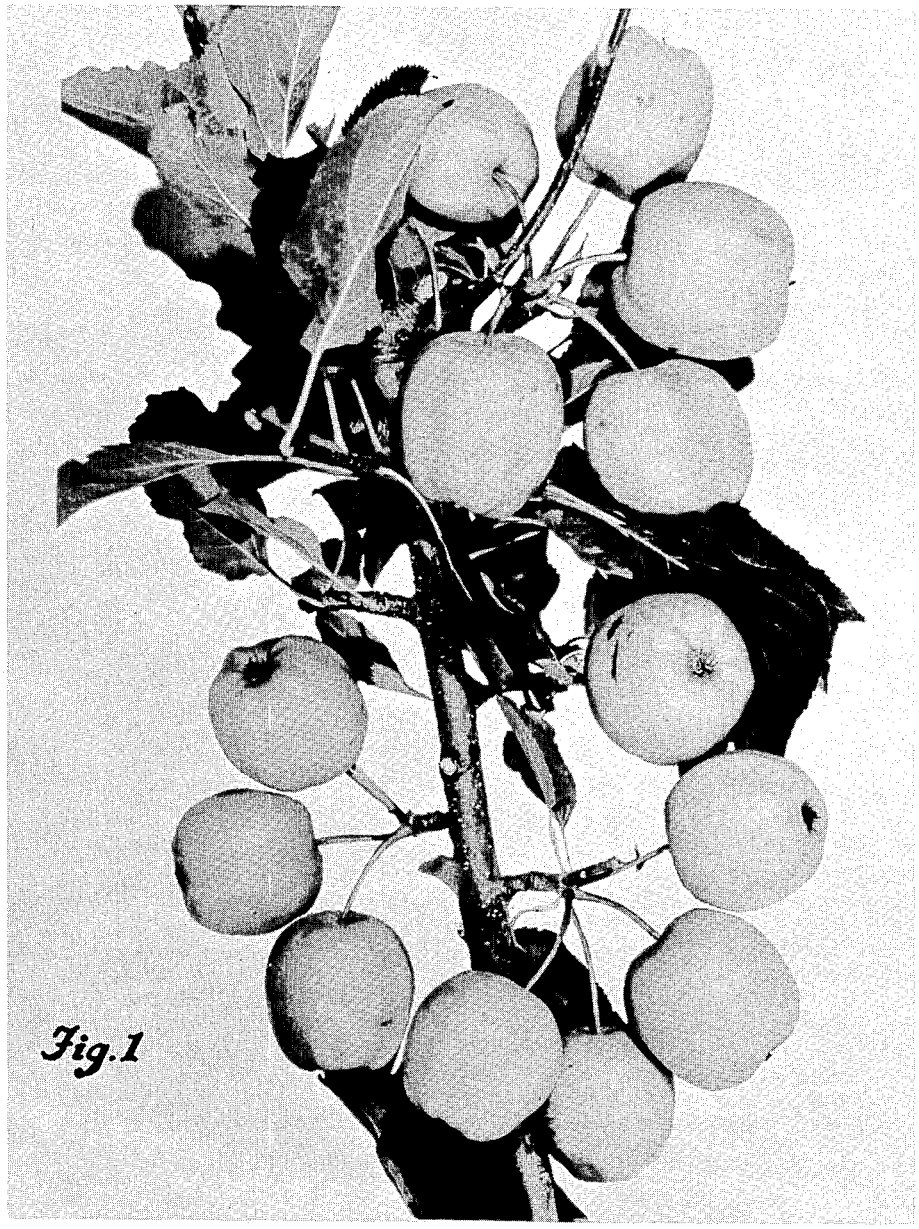
FIGURE 1 is a photograph of a typical fruiting branch of the new variety, illustrating uniformity of fruit size and the relatively large number of fruits (average of 2.8 by actual count) per fruiting cluster compared with Golden Delicious (average of 1.4 by actual count).

FIGURES 3(*a*) and 3(*b*) are photographs of the same branches as shown in FIGURES 2(*a*) and 2(*b*), respectively, with sufficient leaves remaining to show spurring characteristics.

*Trees.*—Medium small; semi-dwarf; moderately vigorous compact form, upright in early years becoming more spreading with age. Height 10 feet; spread 7 feet. Adjacent Golden Delicious of same age: height 13 feet, spread 10 feet. (At Roosevelt, Washington). Trunk of moderate stockiness, smooth. Branches of medium thickness with approximately double the number of spurs per unit of length than Golden Delicious; terminal growth average 8 inches, with adjacent Golden Delicious same age 12 inches.

*Flower and leaves.*—Identical to the standard Golden Delicious.

*Fruits.*—The fruit of my new variety is in every respect similar to standard Golden Delicious in shape, quality, flesh and surface color. The core, carpellary area, and seed are also indistinguishable. Fruit size is more uniform than standard Golden Delicious, and tends to be smaller (due to the greater number of fruit per cluster) under conditions of natural set. When hand-thinned, greater uniformity of fruit size was obtained by completely removing certain clusters and allowing others to remain with their natural set. Using this technique my new sport variety produced 80 percent of its fruits with a transverse diameter between 2¾ and 3 inches (the most desirable market sizes); 15 percent greater than 3 inches and 5 percent smaller than 2¾ inches. Standard Golden Delicious of the same age thinned in the same manner produced 45 percent of its fruit in the 2¾ to 3 inch category, with 35 percent larger than 3 inches in transverse diameter, and 20 percent smaller than 2¾ inches. Axial length-transverse diameter ratio is similar to standard Golden Delicious.

*Comparison.*—The known variety most like my new variety is the apple tree described in Plant Patent No. 2,024, the chief differences being as follows:

(1) A pronounced tendency of my new variety for setting a greater number of fruits per flowering spur as referred to above.

(2) The fruit of my new variety is in every respect similar to that of standard Golden Delicious, whereas that of the variety of Plant Patent No. 2,024 is dissimilar therefrom.

Having thus disclosed my discovery, I claim:

The new and distinct variety of Golden Delicious apple tree, substantially as herein shown and described, charrecterized particularly by its production of fruit like that of standard Golden Delicious, by its medium small, semi-dwarf, upright growth, its large number of spurs per unit of stem length, and its pronounced trait of setting a much greater number of fruits per cluster (i.e., on the average of approximately twice) than on standard Golden Delicious with resultant higher yield of more uniform size fruits.

No references cited.